US006757948B2

(12) United States Patent
Ptchelintsev et al.

(10) Patent No.: US 6,757,948 B2
(45) Date of Patent: Jul. 6, 2004

(54) METHOD FOR MANUFACTURING AN ULTRASONIC ARRAY TRANSDUCER

(75) Inventors: Andrei A Ptchelintsev, Windsor (CA); Roman Gr. Maev, Windsor (CA)

(73) Assignee: DaimlerChrysler Corporation, Auburn Hills, MI (US)

( * ) Notice: Subject to any disclaimer, the term of this patent is extended or adjusted under 35 U.S.C. 154(b) by 0 days.

(21) Appl. No.: 10/361,143

(22) Filed: Feb. 6, 2003

(65) Prior Publication Data

US 2003/0150273 A1 Aug. 14, 2003

Related U.S. Application Data

(60) Division of application No. 09/650,803, filed on Aug. 30, 2000, now Pat. No. 6,546,803, which is a continuation-in-part of application No. 09/471,646, filed on Dec. 23, 1999, now abandoned.

(51) Int. Cl.[7] ................... H04R 17/00; H01L 41/04; H01L 41/08; H01L 41/18
(52) U.S. Cl. .................. 29/25.35; 29/594; 29/417; 29/762; 29/758; 310/334
(58) Field of Search .................. 29/25, 35, 594, 29/827, 417, 412, 426; 310/334, 326, 336; 156/268, 247, 248

(56) References Cited

U.S. PATENT DOCUMENTS

| | | |
|---|---|---|
| 3,384,733 A | 5/1968 | Burbank et al. |
| 3,410,983 A | 11/1968 | Deutsch |
| 3,575,044 A | 4/1971 | Gibbs et al. |
| 3,596,335 A * | 8/1971 | Bennett ............... 29/25.35 |
| 3,726,130 A | 4/1973 | Hurlebaus |
| 3,739,628 A | 6/1973 | Saglio |
| 3,810,385 A | 5/1974 | McFaul et al. |
| 3,868,847 A | 3/1975 | Gunkel |

(List continued on next page.)

FOREIGN PATENT DOCUMENTS

| | | |
|---|---|---|
| GB | 715143 | 3/1953 |
| GB | 774675 | 12/1953 |
| GB | 2 015 159 A | 2/1979 |

(List continued on next page.)

*Primary Examiner*—A. Dexter Tugbang
*Assistant Examiner*—Tai Van Nguyen
(74) *Attorney, Agent, or Firm*—Ralph E. Smith

(57) ABSTRACT

The present invention provides an ultrasonic probe and method for making the same is provided which has an advantageous construction and method of assembly. The ultrasonic probe has a segmented ultrasonic transducer having a plurality of individual independent transducers, a plurality of piezoelectric transducers connected to a first end of a respective individual independent transducer; and a plurality of electrical connections electrically communicating each the piezoelectric transducer with a power source.

9 Claims, 4 Drawing Sheets

U.S. PATENT DOCUMENTS

| | | | |
|---|---|---|---|
| 3,895,685 A | | 7/1975 | Gilette et al. |
| 3,958,451 A | | 5/1976 | Richardson |
| 3,960,005 A | | 6/1976 | Vezina |
| 4,012,946 A | | 3/1977 | Patsey |
| 4,099,045 A | | 7/1978 | Okuda et al. |
| 4,208,917 A | | 6/1980 | Aoyama et al. |
| 4,449,029 A | | 5/1984 | Nied |
| 4,472,620 A | | 9/1984 | Nied |
| 4,480,475 A | | 11/1984 | Tsao et al. |
| 4,530,362 A | | 7/1985 | Hetz |
| 4,596,143 A | | 6/1986 | Norel |
| 4,712,722 A | | 12/1987 | Hood et al. |
| 4,747,192 A | | 5/1988 | Rokurota |
| 4,821,575 A | | 4/1989 | Fujikake et al. |
| 4,894,895 A | | 1/1990 | Rokurohta et al. |
| 5,060,518 A | | 10/1991 | Aleshin et al. |
| 5,099,459 A | * | 3/1992 | Smith .................. 367/153 |
| 5,267,221 A | | 11/1993 | Miller et al. |
| 5,274,296 A | | 12/1993 | Hiki et al. |
| 5,280,724 A | | 1/1994 | Higo et al. |
| 5,296,777 A | | 3/1994 | Mine et al. |
| 5,306,893 A | | 4/1994 | Morris et al. |
| 5,329,498 A | | 7/1994 | Greenstein |
| 5,383,366 A | | 1/1995 | Wallingford et al. |
| 5,439,157 A | | 8/1995 | Geier et al. |
| 5,448,503 A | | 9/1995 | Morris et al. |
| 5,474,225 A | | 12/1995 | Geier et al. |
| 5,486,734 A | | 1/1996 | Seyed-Bolorforosh |
| 5,533,401 A | | 7/1996 | Gilmore |
| 5,537,875 A | | 7/1996 | Viehmann et al. |
| 5,548,564 A | * | 8/1996 | Smith .................. 367/140 |
| 5,592,730 A | | 1/1997 | Greenstein et al. |
| 5,644,085 A | | 7/1997 | Lorraine et al. |
| 5,648,942 A | | 7/1997 | Kunkel, III |
| 5,659,479 A | | 8/1997 | Duley et al. |
| 5,674,415 A | | 10/1997 | Leong et al. |
| 5,677,490 A | | 10/1997 | Gunther et al. |
| 5,744,898 A | * | 4/1998 | Smith et al. ............ 310/334 |
| 5,764,859 A | | 6/1998 | Kim et al. |
| 5,774,376 A | | 6/1998 | Manning |
| 5,814,731 A | | 9/1998 | Alexander et al. |
| 5,834,880 A | * | 11/1998 | Venkataramani et al. ... 310/334 |
| 5,886,454 A | | 3/1999 | Ito et al. |
| 6,116,090 A | | 9/2000 | Maev et al. |

* cited by examiner

METHOD FOR MANUFACTURING AN ULTRASONIC ARRAY TRANSDUCER

PRIORITY CLAIM

This is a divisional of application Ser. No. 09/650,803 filed on Aug. 30, 2000, now U.S. Pat. No. 6,546,803 which is a Continuation-In-Part of Ser. No. 09/471,646 filed on Dec. 23, 1999 (now abandoned).

FIELD OF THE INVENTION

The present invention relates to an ultrasonic array transducer, and more particularly, to an ultrasonic array transducer for non-destructively inspecting a weld joint.

BACKGROUND OF THE INVENTION

Welding is a common process for attaching one metal member to another. This process generally involves heating an interface between the items which are to be welded, thereby melting the interface into one joint or weld nugget. Because this process has its application in many different types of manufacturing, such as automobile manufacturing, inspection ensuring that the weld nugget meets certain quality standards is a must. Specifically, it is desirable to inspect the area, size and configuration of the weld nugget and to determine if any defects exist therein. Uninspected welds may result in weld failure after the welded item is sold or distributed to a final user.

Ideally, a weld is inspected either during or shortly after the welding process so that added inspection does not increase weld time, and to allow weld problems to be identified when they occur. Furthermore, non-destructive testing is preferred so that welded parts which pass inspection may still be sold or distributed to the end user after they have been tested.

Visual inspection systems have been employed in the weld environment for this purpose. Specifically, an individual, such as a quality control person, may gage the size of the weld nugget or destructively test a welded item to determine its internal characteristics.

While weld systems do provide a quantitative analysis of the size of the weld nugget, visual inspection has some drawbacks. First, because of the bright light and harsh conditions generated by welding, visual inspection of a weld cannot be performed during the welding process. Instead, the welded item must be inspected off line, adding more time and cost to manufacturing. Second, to properly inspect the weld for defects, the internal structure of the weld nugget must be observed. This, in many instances, requires the welded item to be destructively tested, rendering the welded item useless. Besides the increased cost associated with scrapping an item for the purpose of inspection, it is practically impossible to destructively test all items. As such, destructive testing results in a lower number of samples tested and increased cost to manufacturing.

Devices and methods developed to inspect welds and other obscured items are generally disclosed in U.S. Patent Applications entitled TRANSDUCER BUILT INTO AN ELECTRODE and MULTIEYED ACOUSTICAL MICROSCOPIC LENS SYSTEM, invented by Maev et al. and assigned to the assignee of the present application and hereby incorporated by reference. While these devices and methods do provide a means for analyzing welded joints, they do not provide the quantitative accuracy sometimes required by manufacturers.

In view of the above, it would be desirable to manufacture an ultrasonic array transducer which is able to non-destructively test a weld subject and which has a high degree of resolution.

SUMMARY OF THE INVENTION

It is therefore an object of the present invention to provide an ultrasonic array transducer able to non-destructively inspect a weld joint.

It is yet another object of the present invention to provide an ultrasonic array transducer which has a high density of acoustical sound generating units for increasing resolution.

In accordance with the broad teachings of this invention, an ultrasonic probe and method for making the same is provided which has an advantageous construction and method of assembly. The ultrasonic probe has a segmented ultrasonic transducer having a plurality of individual independent transducers, a plurality of piezoelectric transducers connected to a first end of a respective individual independent transducers, and a plurality of electrical connections electrically communicating each the piezoelectric transducer with a power source.

In another aspect of the present invention, the power source comprises a pulser-receiver in electrical communication with a multiplexer. The multiplexer, in turn, is in electrical communication with the plurality of piezoelectric transducers. The pulser-receiver is responsive to the multiplexer to provide a display representative of acoustical images received by the piezoelectric transducers.

Further areas of applicability of the present invention will become apparent from the detailed description provided hereinafter. It should be understood that the detailed description and specific examples, while indicating preferred embodiments of the invention, are intended for purposes of illustration only, since various changes and modifications within the spirit and scope of the invention will become apparent to those skilled in the art from this detailed description.

BRIEF DESCRIPTION OF THE DRAWINGS

In the drawings which illustrate the best mode presently contemplated for carrying out the present invention.

DETAILED DESCRIPTION OF THE PREFERRED EMBODIMENTS

The following description of the preferred embodiments is merely exemplary in nature and is in no way intended to limit the invention, its application, or uses.

Figure 1:
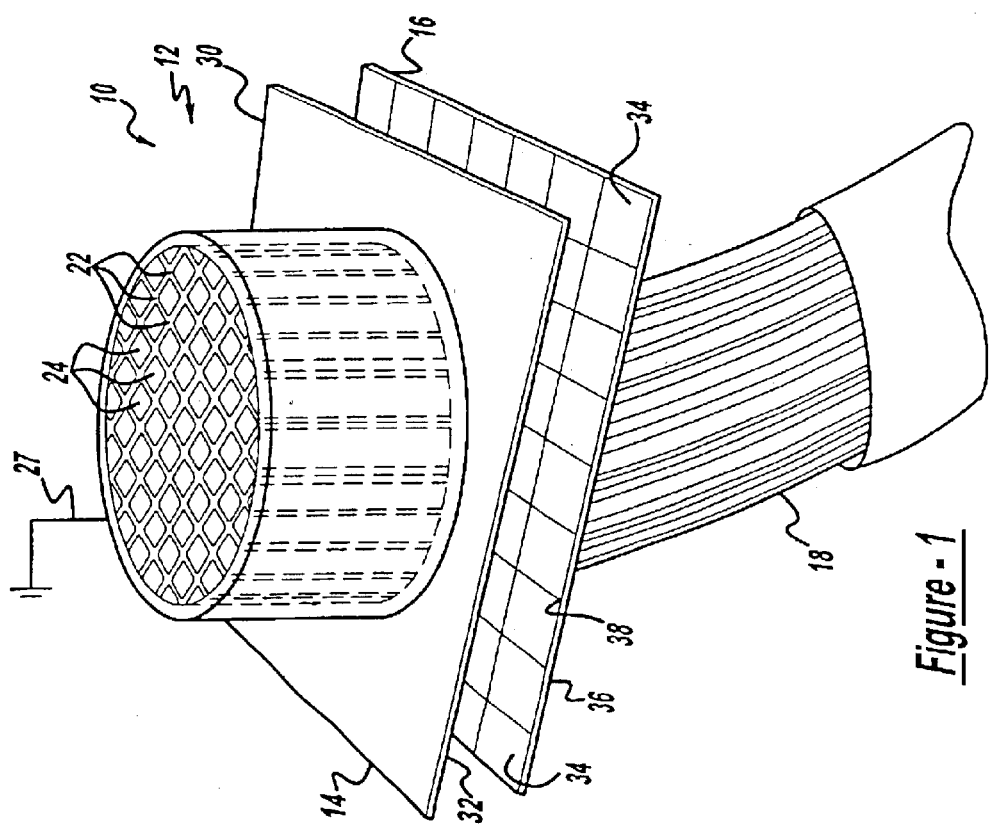
FIG. 1 is an exploded view of an ultrasonic array transducer according to the present invention.

Referring now to FIG. 1, an exploded view of an ultrasonic array transducer 10 is shown. Ultrasonic array transducer 10 generally comprises a segmented ultrasonic transducer 12, Z-axis conductive pad 14, circuit interface board 16, and coaxial cable 18.

Segmented ultrasonic transducer 12 generally has a cluster (or clusters) of small individual independent transducers 24, which are separated by a plurality of gaps 22. Each gap 22 (also called a "kerf") is filled with a non-conductive bonding agent which maintains the elements bonded together and electrically insulates them from each other.

Figure 6:
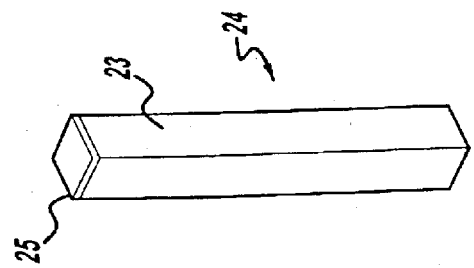
FIG. 6 is a perspective view of an individual independent transducer for an ultrasonic array transducer according to the present invention.

FIG. 6 illustrates one individual independent transducer 24. Individual independent transducer 24 is composed of an ultrasonic element, such as piezoelectric crystal 25 (or may be any other ultrasonic element), and a matching damping body 23. Each piezoelectric transducer, when actuated, generates an ultrasonic pulse. The generation of this ultrasonic pulse is due to a physical reaction to electrical stimuli as is known in the art.

The remainder of individual independent transducer 24 is damping body 23. Damping body 23 is designed to make an ultrasonic pulse generated by individual independent transducer 24 broadband. The broadband wave ensures that a definable wave front, having a sharp acoustic signature, exits each individual independent transducer 24. Damping body 23 accomplishes this by the mere fact of its weight. The weight of damping body 23 changes the vibration characteristics of piezoelectric crystals (which will be described) which are attached to it. Specifically, piezoelectric crystals which are attached to damping body 23 vibrate in response to acoustical energy in such a way as to provide a greater definable wave front.

Damping body 23 is preferably constructed from a mixture of glue and a high percentage of heavy conductive powder. The glue acts to retain the conductive powder in a solid and rigid structure. The glue is mixed with the conductive powder in such a way as to ensure that some glue is in contact with the piezoelectric crystal 25. This glue forms the bond between damping body 23 and piezoelectric crystal 25. A layer of conductive material, preferably a thin conductive coating, is coated on the exposed surface of piezoelectric crystal 25. This layer extends along the entire surface of ultrasonic probe 10 and provides a grounding circuit therefore (as will be discussed in greater detail).

Z-axis conductive pad 14, as is known in the art, provides a plurality of conductive paths from one element such as a circuit board to a second element. In the present invention, Z-axis conductive pad 14 provides a plurality of conductive paths from piezoelectric crystal 25 to circuit interface board 16.

Circuit interface board 16 is divided into a plurality of areas 34. Each area 34 combines with a respective area on z-axis conductive pad 14 to form a plurality of conductive paths having the closest possible resemblance with the cross section of the segmented ultrasonic matrix 10. Thereby, each path communicates with a respective individual independent transducer 24.

Each coaxial cable 18 is connected to a different area 34 of lower face 36 of circuit interface board 16, preferably by soldering. This connection, in conjunction with the other electrical connections discussed above, allows each coaxial cable 18 to provide electrical power to a respective side of piezoelectric crystal 25 which is opposite damping body 23. As such, power supplied by coaxial cable 18 actuates piezoelectric crystal 25 electrically communicates with damping body 23 to ground through the layer of conductive material on piezoelectric crystals 25. It is noted that coaxial cable 18 can connect to circuit interface board 16 by a conductive layer that is a soft printed circuit board ribbon conductor.

Figure 2:
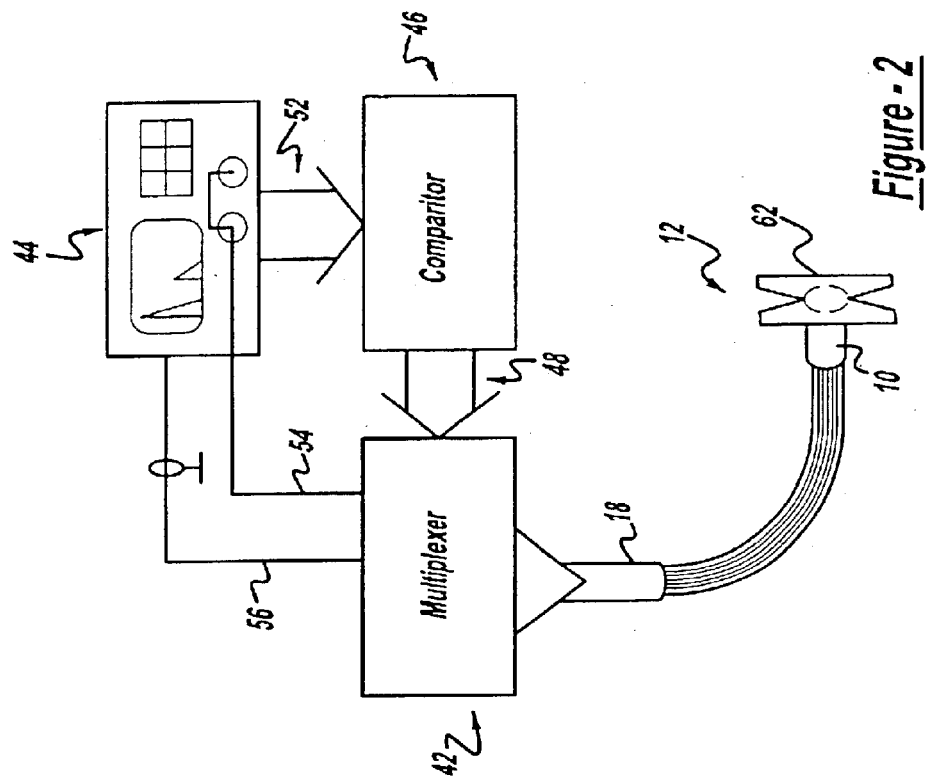
FIG. 2 is a schematic view of an ultrasonic probe and data acquisition system for an ultrasonic array transducer according to the present invention.

Referring now to FIG. 2, a fully assembled ultrasonic array transducer 10 is shown including multiplexer 42, pulser-receiver 44, and computer 46. Segmented ultrasonic transducer 12 is connected to multiplexer 42 through cable assembly 18. Multiplexer 42, in turn, communicates with pulser-receiver 44 by connections 54 and 56. Pulser-receiver 44 communicates with computer 46 through serial interface 52. Finally, computer 46 is electrically attached to multiplexer 42 by parallel port connection 48. It is noted, however, that computer 46 can also communicate with multiplexer 42 through serial interface 52 and with pulser-receiver 44 through parallel port connections 48 or through any other possible interface.

With continued reference to FIGS. 1 and 2, the operation of the present invention will now be described. Welded item 62 is first positioned under ultrasonic probe 10. Ultrasonic probe 10 can be connected to the surface of the welded item in a number of ways, such as via solid or liquid delays or soft elastomeric delays or in direct contact without delays. Preferably however, before ultrasonic probe 10 is placed in physical contact with welded item 62, an ultrasonic gel is layered between the two elements to increase the efficiency which sound generated from piezoelectric crystal 25 is transferred to welded item 62. Computer 46 next instructs pulser-receiver 44 to send an electrical pulse to multiplexer 42. Computer 46 instructs multiplexer 42 to send this pulse to a specific wire 18 corresponding to a specific individual independent transducer 24. The signal travels from one of the wires of cable assembly 18, through an area 34 of circuit interface board 16 and through Z-axis conductive pad 14 to a respective individual independent transducer 24. This electrical signal is ultimately grounded by traveling across the conductive coating on piezoelectric crystals 25 and out to grounding connection 27. Piezoelectric crystal 25 generates an acoustical pulse, in response to the electrical signal, which propagates toward welded item 62. Acoustic energy reflected from welded item 62 oscillates piezoelectric crystal 25, thereby inducing a current back into wire 18. This process is repeated for each piezoelectric crystal 25 until all individual independent transducers 24 have been fired. The received signals from individual independent transducers 24 are interpreted by pulser-receiver 44 to develop a plurality of A-scans, one A-scan per individual independent transducer 24. Computer 46 then compiles all of the generated A-scans from pulser-receiver 44 and develops a C-scan therefrom. A method for sequentially firing all piezoelectric transducers 28 and analyzing signals received therefrom to form A-scans and subsequent C-scans is generally disclosed in U.S. patent application Ser. No. 09/303,301 filed Apr. 30, 1999, and entitled MULTIEYED ACOUSTICAL MICROSCOPIC LENS SYSTEM, invented by Maev, et al. assigned to the assignee of the present application, and hereby incorporated by reference.

It is noted, however, various possible modes of operation are available for the present invention. Such modes include through-transmission, pitch-catch, tandem and other modes. In such modes, two ultrasonic transducers are used. Preferably, one transducer is a standard monolithic transducer and the other is an ultrasonic array transducer 10 as described above. Generally, the monolithic transducer is used for transmission by creating a distribution of acoustic energy that passes through the welded item, as modified by the welded item's geometry, material properties, and flows, and is received by the ultrasonic array transducer 10. The ultrasonic array transducer 10 then reads the acoustic energy and provides a means for visual presentation of the characteristics of the welded item, whereby nondestructive characterization of the welded item is possible. In addition, the standard monolithic transducer can be positioned directly on top of the individual independent transducers 24, opposite the Z-axis conductive pad 14.

Figure 9:
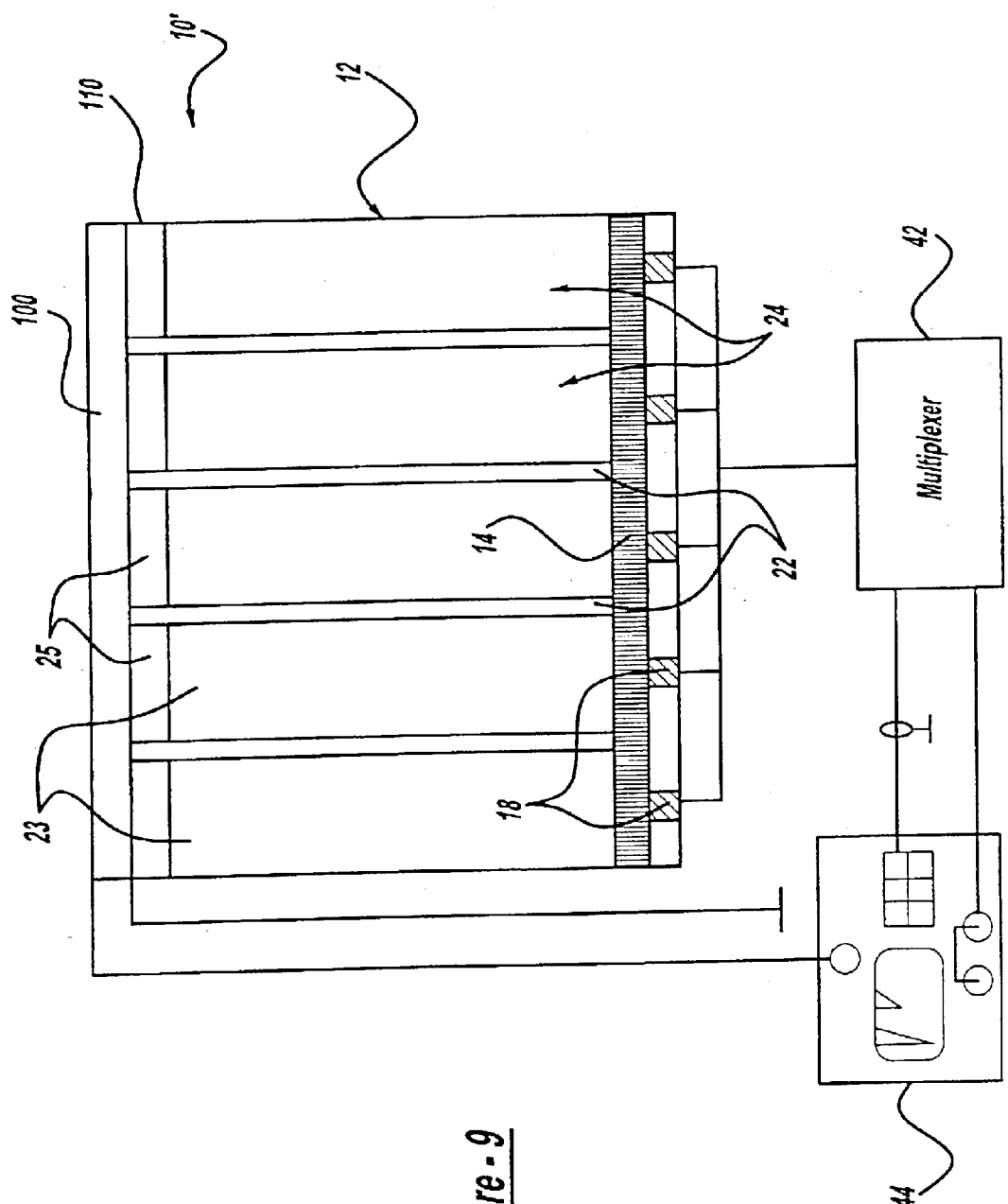
FIG. 9 is a schematic view of an ultrasonic probe and data acquisition system for an ultrasonic array transducer according to an alternative embodiment of the present invention.

Another mode of operation is enabled by a variation of the ultrasonic array transducer 10' including a segmented ultrasonic transducer 12 having a cluster of independent transducers 24 separated by gaps 22 filled with a non-conductive bonding agent, combined with monolithic piezoelectric element 100 installed adjacent the ultrasonic array within a housing 110, as shown in FIG. 9. Each transducer 24 preferably includes a piezoelectric crystal 25 (or other ultrasonic element) and a damping body 23. The monolithic piezoelectric element 100 is connected to the pulse-receiver 44, which communicates a burst of ultrasonic energy through the ultrasonic array transducer 10' and to the welded item. The transducers 24 act as a multi-element receiver producing a map of the field useable for various purposes such as imaging, monitoring, and measurement. Preferably, a plurality of coaxial cables 18 are connected to a Z-axis conductive pad 14 for transmitting the acoustic signal to the multiplexer 42. Alternatively, a soft-printed circuit board ribbon conductor can be used in place of the plurality of coaxial cables 18.

Other modes of operation are disclosed in U.S. patent applications Ser. No. 09/283,397, filed Apr. 1, 1999, entitled TRANSDUCER BUILT INTO AN ELECTRODE and Ser. No. 09/303,301, filed Apr. 30, 1999, and entitled MULTI-EYED ACOUSTICAL MICROSCOPIC LENS SYSTEM, both invented by Maev et al., assigned to the assignee of the present application, and hereby incorporated by reference.

Figure 5:
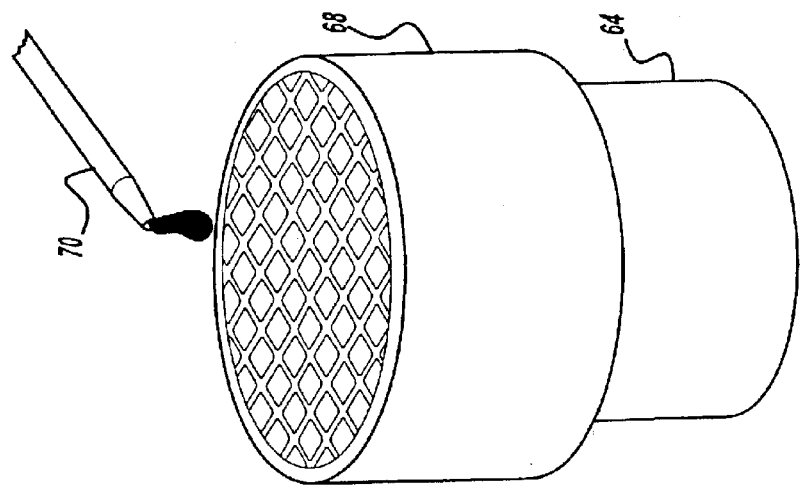
FIG. 5 is a perspective view of a diced ultrasonic probe being filled with nonconductive compound for electrical and acoustic insulation according to the present invention.
Figure 4:
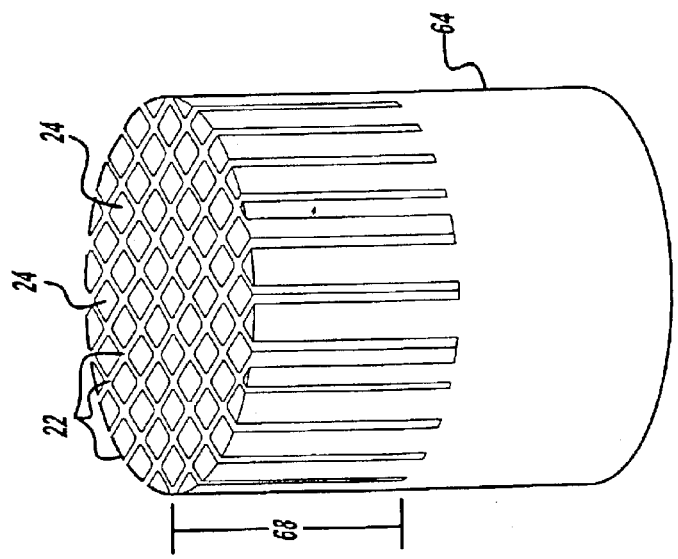
FIG. 4 is a perspective view of a diced ultrasonic probe for an ultrasonic array transducer according to the present invention.
Figure 3:
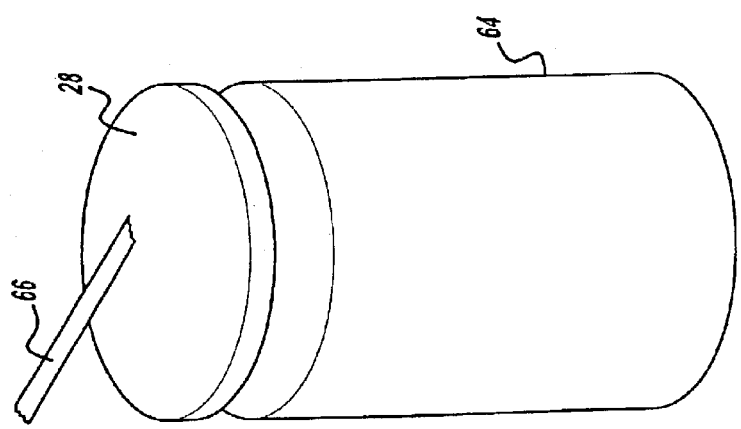
FIG. 3 is a perspective view of an ultrasonic probe prior to dicing for an ultrasonic array transducer according to the present invention.
Figure 8:
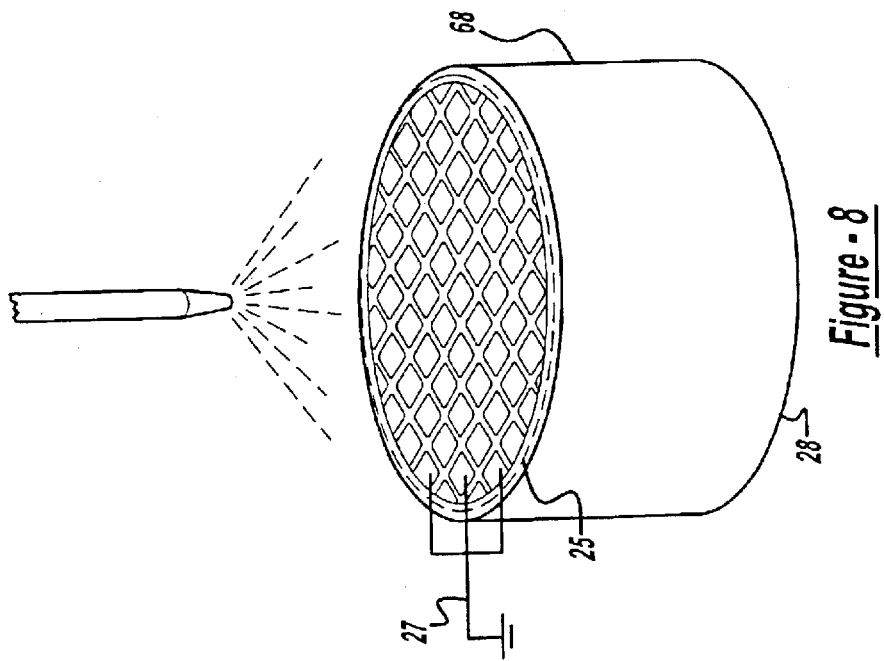
FIG. 8 is a perspective view of an ultrasonic probe being coated with a conductive material according to the present invention.
Figure 7:
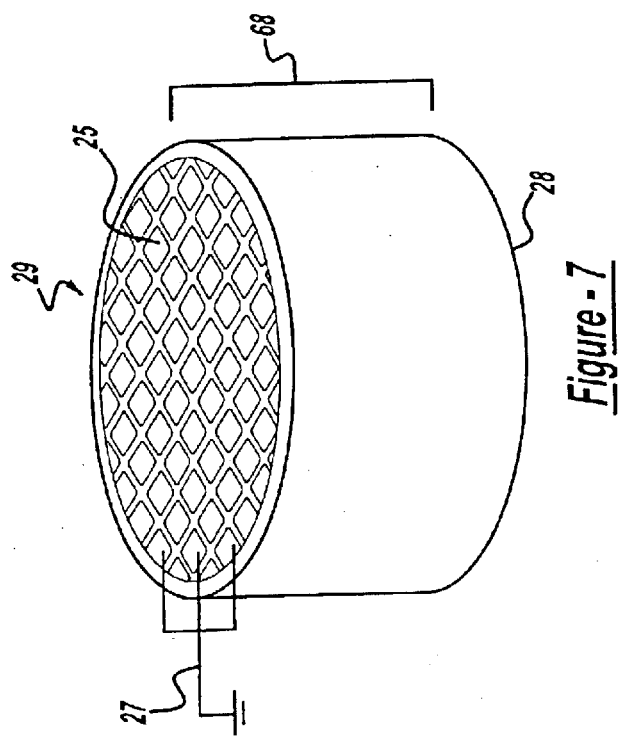
FIG. 7 is a perspective view of an ultrasonic probe connected to a grounding connector according to the present invention.

Referring to FIGS. 3–5, 7 and 8, the assembly of the present invention will now be described. In FIG. 3, a cylindrical uniformly shaped piece of damping material 64 is shown with a wire saw 66 and piezoelectric crystal 25 positioned over it. Such uniform shapes include cylinders, rectangles, ellipses, triangles and all other shapes which can be sliced up and down to form a plurality of smaller width, yet similarly shaped, elements. Piezoelectric crystal 25 is disc like in shape and matches the geometrical configuration of damping material 64. In the first operation, piezoelectric crystal 25 is attached to damping material 64 through a molding process and preferably uses the glue in the buffer material 64 for attachment. Next, ultrasonic buffer material 64 is sawed in a criss-cross fashion by wire saw 66. As shown in FIG. 4, this sawing extends downward a length 68 within the material and forms gaps 22. The configuration of the gaps 22 define the outer bounds of each individual independent transducer 24. As shown in FIG. 5, harness 68 is then positioned around the cut portion of ultrasonic buffer material 64. Harness 68 acts to encapsulate the newly formed individual independent transducers. Then, an epoxy or other bonding agent which is electrically and mechanically insulating is poured into gaps 22 by nozzle 70. This epoxy ensures that each individual independent transducer is electrically insulated from the remaining individual independent transducers and acts to keep the individual independent transducers 24 together in a fixed configuration. After the epoxy cures, the sawed portion of ultrasonic damping material 64 is separated from the unsawed portion. Grounding connections 27 are attached to the exposed ends of a few piezoelectric crystals 25. Referring now to FIG. 8, a coating of conductive material, preferably Al or Au is sprayed over the surface of the exposed sides of piezoelectric crystals 25. This coating acts to provide a conductive layer which connects each respective end of piezoelectric crystal 25 along side 29 with grounding connection 27.

Coaxial cables 18, containing a plurality of wires, is then attached to circuit interface board 16. Each wire of coaxial cable 18 is bonded to each area 34 of circuit interface board 16. Z-axis conductive pad 14 is then positioned between circuit interface board 16 and segmented ultrasonic transducer 12. Z-axis conductive pad 14, circuit interface board 16 and individual independent transducer 24 is then sandwiched together, thereby providing electrical passage from each respective wire of coaxial cable 18 and area 34 to a resulting individual independent transducer 24. It is noted that preferably only a frictional engagement exists between z-axis conductive pad 14 and the other sandwiched elements. This sandwiching eliminates the requirement that each element must be mechanically attached by solder or other affixing method. A shell or other form of housing can then be placed around the resultant ultrasonic probe 10.

The invention being thus described, it will be obvious that the same may be varied in many ways. Such variations are not to be regarded as a departure from the spirit and scope of the invention. Such variations or modifications, as would be obvious to one skilled in the art, are intended to be included within the scope of the following claims.

What is claimed is:

1. A method for manufacturing an ultrasonic array transducer, said method comprising the steps of:

providing a uniformly shaped piece of damping material;

attaching a plezoelectric material to a first end of said damping material;

segmenting said damping material and said plezoelectric material parallel to and along a first length to form a plurality of individual independent transducers along said length, each said individual independent transducer including a plezoelectric crystal bonded to a damping body, whereby each of said plurality of individual independent transducers being separated from a remainder of said individual independent transducers by a plurality of gaps;

filing said plurality of gaps with a non-conductive bonding agent, whereby said non-conductive bonding agent electrically insulates mechanically bonds each of said plurality of individual independent transducers to a remainder of said plurality of individual independent transducers; and separating said plurality of individual independent transducers from a non-segmented remainder of said damping material.

2. The method as claimed in claim 1, further comprising the step of connecting each of said plurality of individual independent transducers to a power source by a connector and grounding each individual independent transducer by a grounding connection, said connecting step occurring after said plurality of individual independent transducers are segmented from said non-segmented remainder of said damping material, said connector providing an independent electrical path from said power source to each said individual independent transducer.

3. The method as claimed in claim 2, wherein the step of electrically connecting each of said plurality of individual independent transducers to a power source, comprises:

providing a cable assembly having a plurality of wires and a circuit interface board, each wire of said cable assembly having a first end and a second end;

electrically connecting said first end of said cable assembly to a respective portion of said circuit interface board on a first side of said circuit interface board;

electrically connecting said first end of each of said cable assembly to said power source;

electrically connecting each portion of said circuit interface board along a second side of said circuit interface board to a respective damping body;

connecting each said damping body to a piezoelectric crystal on one of said plurality of individual independent transducers; and wherein said connector comprises said cable assembly and circuit interface board.

4. The method as claimed in claim 3, wherein said connector further includes a Z-axis conductive pad, said Z-axis conductive pad being sandwiched between said circuit interface board and said plurality of individual independent transducers, said Z-axis conductive pad electrically connecting each portion of said circuit interface board to a respective individual independent transducer.

5. The method as claimed in claim 1, wherein said uniformly shaped ultrasonic material is segmented by a wire saw.

6. The method as claimed in claim 1, wherein said uniformly shaped damper material is cylindrically shaped.

7. The method as claimed in claim 1, wherein said damper material is constructed from a composite of glue and conductive material.

8. The method as claimed in claim 3, wherein said step of connecting each said damping body to a grounding connection further comprises the steps of:

coating a second end of said individual independent transducers with a conductive material, said second end being located proximate to said piezoelectric crystals, attaching said grounding connection to said second end of at least one of said individual independent transducers, whereby said conductive material provides a conductive path from said second end of each of said individual independent transducers to said grounding connection.

9. The method as claimed in claim 8, wherein said conductive coating is a member of the set consisting of Au and Al.

* * * * *